United States Patent [19]

Akkapeddi et al.

[11] Patent Number: 5,276,131
[45] Date of Patent: Jan. 4, 1994

[54] PREPARATION OF POLYAMIDE FROM ARYLENE CYCLIC DIAMIDE

[75] Inventors: Murali K. Akkapeddi; Jeffrey H. Glans, both of Morristown, N.J.

[73] Assignee: Allied Signal Inc., Morris Township, Morris County, N.J.

[21] Appl. No.: 896,934

[22] Filed: Jun. 11, 1992

[51] Int. Cl.$^5$ ............................................... C08G 69/00
[52] U.S. Cl. .............................. 528/271; 428/474.4; 528/322; 528/335; 528/338; 528/339; 528/340; 528/344; 528/347; 528/367; 540/1
[58] Field of Search .............. 528/271, 335, 347, 322, 528/338, 339, 340, 344, 367

[56] References Cited

U.S. PATENT DOCUMENTS

| | | |
|---|---|---|
| 2,752,328 | 6/1956 | Magat . |
| 3,382,216 | 5/1968 | Blaschke et al. . |
| 3,696,074 | 10/1972 | Tsuda et al. . |
| 3,917,561 | 11/1975 | Chapman et al. . |
| 4,400,490 | 8/1983 | Yang . |
| 4,863,991 | 9/1989 | Poppe et al. . |
| 5,079,339 | 1/1992 | Akkapeddi et al. . |

OTHER PUBLICATIONS

"On Understandin Macrocyclic Ring Systems" Stetter et al., Chem. Berichte, 91, pp. 1775-1781 (1958).
"Preparation and Polymerization of Bisphenol A Cyclic Oligomeric Carbonates" Brunelle et al., Macromolecules, 1991, pp. 3035-3044.

*Primary Examiner*—Harold D. Anderson
*Attorney, Agent, or Firm*—Roger H. Criss

[57] ABSTRACT

This invention relates to cyclic diamides that are readily polymerized to form poly(terephthalamides). The resulting poly(terephthalamides) have high crystallinity, high temperature capabilities, dimensional stability, low moisture sensitivity, and solvent and chemical resistance.

5 Claims, No Drawings

PREPARATION OF POLYAMIDE FROM ARYLENE CYCLIC DIAMIDE

BACKGROUND OF THE INVENTION

1. Field of the Invention

The present invention relates to monomers of high temperature polyamides. Particularly, the present invention relates to cyclic terephthaldiamides that polymerize to form poly(terephthalamides).

2. Description of the Prior Art

The chemistry of polymerization of cyclic monomers or oligomers is well known in the polymer art. Such cyclic monomer polymerization processes have been utilized in polyamide applications, particularly for reaction injection molding (RIM) applications. Typically, in such a polymerization application, an anhydrous lactam (cyclic amide) is in-situ polymerized at or above 100° C. in the presence of one or more of basic catalysts such as alkali and alkaline earth metals, their hydrides, hydroxides, alkoxides, oxides, alkyls or amides. Various lactams having 6–12 carbon atoms, such as caprolactam, pyrrolidone, piperidone, valerolactam and lauryllactam, have been known to be useful for in-situ polymerization processes. The advantage of the in-situ polymerization processes of lactam monomers, such as RIM, is based on the fact that the monomers employed are low melting and the polymers resulting therefrom are high melting and highly crystalline, and the polymerization process does not produce any byproducts. In addition, lactam monomers have low melt viscosity, obviating the need to utilize high pressure equipments necessary in conventional melt-injection molding processes.

Although the polyamides resulting from the above-mentioned process exhibit a range of valuable properties, they have disadvantages in that they are dimensionally unstable, because of their inherent hygroscopic property, and have limited high-temperature capabilities. Therefore, it is desirable to provide monomers or oligomers of polyamides that can be in-situ polymerized and have improved dimensional stability and high-temperature capability.

The polyamides derived from terephthalic acid and alkanediamines, which are commonly referred in the art as poly(terephthalamides), have been known in the art to exhibit high melting point and low moisture sensitivity. However, the high melting point of poly(terephthalamides), which is higher than 300° C. and practically coincides with the thermal decomposition temperature of the polyamides, renders the production of the polymers by the conventional melt polymerization process unpracticable. Various publications have disclosed various methods of overcoming this polymerization difficulty. For example, U.S. Pat. No. 2,752,328 to Magat; U.S. Pat. No. 3,382,216 to Blaschke et al.; and U.S. Pat. No. 3,696,074 to Tsuda et al. disclose terephthalamide copolymer compositions having a lower crystalline morphology than homopolymer terephthalamides. Although such terephthalamide copolymers are melt. processible, they do not retain the benefits of crystalline polymers such as solvent resistance and various high temperature utilities including high heat deflection temperature. Therefore, it is desirable to produce poly(terephthalamides) of high crystallinity that have high temperature capabilities, dimensional stabilities and low moisture sensitivity, and to provide monomers of such poly(terephthalamides) that can be polymerized without utilizing the conventional polymerization processes which may thermally decompose the resulting poly(terephthalamides).

Stetter et al. disclosed in their article, "On Understanding Macrocyclic Ring System", Chem. Berichte, 91, 1775–1781 (1958), a range of macrocyclic diamides from aromatic dicarboxylic acids including 2,5-diaza-1,6-dioxo-[6](1,2)-orthocyclophane; 2,7-diaza-1,8-dioxo-[8](1,2)-orthocyclophane; 2,9-diaza-1,10-dioxo-[10](1,2)-orthocyclophane; 2,7-diaza-1,8-dioxo-[8](1,3)-metacyclophane; 2,9-diaza 1,10-dioxo-[10](1,3)-metacyclophane; 2,9-diaza-1,10-dioxo-[10](1,4)-paracyclophane; 2,11-diaza-1,12-dioxo-[12](1,4)-paracyclophane; 2,13-diaza-1,14-dioxo-[14](1,4)-paracyclophane; 1,1'-diaza-2,2'-dioxo-[2,2](1,2)-orthocyclophane; and 3,3'-diaza-4,4'-dioxo-[6,6](1,4)-paracyclophane. Of these cyclophanes, 2,11-diaza-1,12-dioxo-[12](1,4)-paracyclophane and 2,13-diaza-1,14-dioxo-[14](1,4)-paracyclophane exhibit molecular configurations that may polymerize. However, Stetter et al. did not recognize any use for the macrocyclic diamides they had synthesized.

SUMMARY OF THE INVENTION

In accordance with the present invention, there is provided a cyclic diamide according to the following structure:

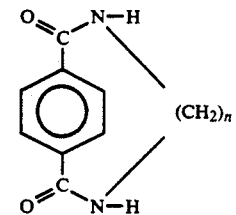

wherein n is 12 or 14.

Also in accordance with the present invention, the cyclic diamides are polymerized to produce poly(terephthalamides) by a method comprising the steps of reacting 1,12-dodecanediamine or 1,14-tetradecanediamine with acid chloride of terephthalic acid to form a cyclic diamide at a temperature below the melting point of the resulting cyclic diamide and then heating the cyclic diamide to a temperature between the melting point of the cyclic diamide and about 330° C.

In addition, there is provided in accordance with the present invention a method of producing a poly(terephthalamide) coated article comprising the steps of melting a cyclic diamide selected from the group consisting of 2,15-diaza-1,16-dioxo-[16]-(1,4)-paracyclophane and 2,17-diaza-1,18-dioxo-[18]-(1,4)-paracyclophane; contacting an article with the melted cyclic diamide to form a coating; and exposing the cyclic diamide coated article to a temperature between the melting point of the cyclic diamide and 330° C. to polymerize the cyclic diamide and to fuse the resulting poly(terephthalamide) onto the article.

DETAILED DESCRIPTION OF THE INVENTION

The present invention provides cyclic diamides that are suitable for in-situ polymerization applications. The cyclic diamides of the present invention have the following structure:

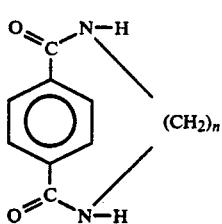

wherein n is 12 or 14, and they may be referred as 2,15-diaza-1,16-dioxo-[16](1,4)-paracyclophane and 2,17-diaza-1,18-dioxo-[18](1,4)-paracyclophane, respectively.

The cyclic diamides of the present invention may be synthesized by the condensation reaction of the acid chloride or acetate, preferably acid chloride, of terephthalic acid with a n-alkylene diamine having 12 or 14 carbon atoms, i.e., 1,12-dodecanediamine or 1,14-tetradecanediamine, at a temperature substantially below the melting point of the resulting cyclic diamides. The condensation reaction is conducted in an aprotic anhydrous solvent, such as chlorinated hydrocarbons, e.g., chloroform, methylene chloride and tetrachloroethane; aliphatic ethers, e.g., tetrahydrofuran and diethyl ether; and hydrocarbons, e.g., benzene, toluene and hexane, preferably chlorinated hydrocarbons, more preferably chloroform, at a temperature between about 0° C. and about 100° C., preferably between about 5° C. and about 30° C. The cyclic diamide preparation preferably is performed at a high dilution to minimize the production of linear oligomers and small polymers of different chain-lengths.

The resulting diamides readily undergo rapid polymerization when they are exposed to a temperature above the melting point of the diamides. However, the polymerization temperature must not be above the thermal degradation point of the resulting polyamides, which in general is above about 330° C. Preferably, the polymerization of the cyclic diamides of the present invention is conducted in a temperature range from about 275° C. to about 320° C. It has been unexpectedly found that, unlike the prior art polymerization of cyclic monomers and oligomers, the polymerization does not require any external catalysts.

The polymerization, in accordance with the present invention, of 2,15-diaza-1,16-dioxo-[16]-(1,4)-paracyclophane and 2,17-diaza-1,18-dioxo-[18](1,4)-paracyclophane produces poly(dodecane terephthalamide), otherwise known in the art as nylon 12T, and poly(tetradecane terephthalamide), known as nylon 14T, respectively. As is known in the art these polyamides polymerized from the cyclic diamides of the present invention are highly crystalline, dimensionally stable, highly temperature and chemical resistant polyamides.

In addition, the poly(terephthalamides) of the present invention may contain up to 30 mol %, of a metacyclic diamide synthesized in accordance with the above-mentioned synthesis process for the cyclic diamides utilizing isophthalic acid and a n-alkylene diamine having 10 to 14 Carbon atoms, i.e., 1,10-decanediamine; 1,12-dodecanediamine or 1,14-tetradecanediamine. The resulting metacyclic diamides may be referred as 2,13-diaza-1,14-dioxo-[ 14](1,3)-metacyclophane; 2,15-diaza-1,16-dioxo-[16](1,3)-metacyclophane; and 2,17-diaza-1,18-dioxo-[18](1,3)-metacyclophane, respectively. The suitable metacyclic diamide of the present invention may also be synthesized from other aromatic dicarboxylic acids such as t-butyl isophthalic acid and phenylindane dicarboxylic acid. It is believed that the addition of the metacylic diamides decreases the melting point of the resulting polyamide without significantly sacrificing other physical and chemical properties of the poly(terephthal-amides) of the present invention.

The polyamides polymerized from the cyclic diamide of the present invention are suitable for use in a wide variety of applications in which high temperature capability, dimensional stability, chemical and solvent resistance are required. Non-limiting examples of such useful applications are magnet wires coating, electrical conductor jacketing, glass fiber or fabric coating, carbon fiber or fabric coating and various RIM applications.

Magnet wire, which is an insulating-material coated wire used in coil form for the production of magnetic fields, is used in the construction of motor windings, relay coils, transformers, lighting ballasts, automotive generators and the like. A number of different synthetic enamel coating systems are being used in the industry, including nylon 66, polyurethane, polyvinyl formal and acrylic formulations. The advantageous polymerization characteristics of the present cyclic diamides, including rapid polymerization kinetics and byproduct-free polymerization, and relatively low melt viscosity of the cyclic diamide, as well as the advantageous properties of the resulting polymer, including high temperature capability, excellent abrasion resistance, chemical and solvent resistance and low-moisture absorption property, make the cyclic diamide an excellent magnet wire coating material.

Magnetic wires can be coated with the cyclic diamides of the present invention in a variety of coating methods conventionally known in the art. One such suitable method is coating a melted cyclic diamide of the present invention by either extruding or spraying onto an uncoated wire and then exposing the coated wire to an elevated temperature which is sufficiently high enough to polymerize the diamide and to fuse the resulting polymer over the wire. As such, the polymerizing and fusing temperature must be sufficiently high enough not only to polymerize the cyclic diamide but also to melt-fuse the resulting polymer. As mentioned above, most polyamides thermally decompose at a temperature higher than about 330° C. Consequently, the resulting polymer must have a melting point below the decomposition temperature. In this respect, the cyclophane cyclic diamides disclosed in the above-mentioned article by Stetter et al., except 2,13-diaza-1,14-dioxo-[14](1,4)-paracyclophane which is believed to be polymerizable, are not suitable cyclic diamides in accordance with the present invention in that some of the disclosed diamides may not polymerize, and some that do polymerize do not have high crystalline structures or have melting point at or above the thermal decomposition point of the polyamides rendering the diamides unusable, i.e., the resulting polymer decomposes before it can be fused.

In accordance with the coating procedure disclosed above, the cyclic diamides of the present invention can also be utilized for electrical conductor jacketing and glass or carbon fiber coating applications.

The cyclic diamides of the present invention can be polymerized by heating the diamides above their melting points to provide crystalline terephthalamides having high temperature capability, dimensional stability, low moisture sensitivity, and solvent and chemical resistance. Furthermore, it has been found that the cyclic diamides disclosed herein rapidly polymerize without the need for the addition of external catalysts.

The following example is provided to illustrate the present invention and it should not be construed in any way to limit the scope of the present invention.

EXAMPLE

Terephthaloyl chloride, available from Aldrich Chemical Company, and 1,12-dodecanediamine, available from DuPont were sublimed before use. Chloroform was freshly distilled from phosphorous pentoxide. A dual syringe pump, Model 22, from Harvard Apparatus (South Natick, Mass.) was used for the simultaneous addition of monomers.

Preparation of 2,15-diaza-1,16-diox-[16]-(1,4)-paracyclophane:

A solution of 2.00 g (9.98 mmol) of freshly sublimed 1,12-dodecanediamine in 45 ml of chloroform was taken up in a 50 ml gas tight syringe. A solution of 2.03 g (10.0 mmol) of terephthaloyl chloride in 45 ml of chloroform was taken up in a second syringe. A dual syringe pump was used to add these solutions to a 2 liter, 3-neck flask containing 3.0 ml (21.5 mmol) of triethylamine in 800 ml of chloroform. The two solutions were added simultaneously at 10 ml/min. A white precipitate slowly formed during the course of the addition. The reaction mixture was allowed to stir at room temperature overnight.

The resulting precipitate was filtered and the filtrate was washed with water and 10% potassium carbonate. The washed filtrate was dried over MgSO$_4$. The filtered solid was extracted overnight with hot chloroform in a Soxhelt extraction apparatus. The resulting chloroform solution was combined with the dried filtrate and reduced to give 2.38 g (85% yield) of an off-white solid.

The combined fractions were recrystallized from chloroform to give 1.71 g (52% yield) of a white solid having a melting point range of 272°–273° C.

Polymerization of 2.15-diaza-1,16-dioxo-[16]-(1,4)-para-cyclophane:

A 16×180 mm polymerization tube was charged with 0.49 g (1.48 mmol) of the above cyclic diamide, vacuum purged with nitrogen for three times, and placed in a 300° C. oil bath for 40 min. The reaction mass was allowed to cool and the resulting plug of polymer was dissolved in concentrated sulfuric acid. This solution was filtered and precipitated into water. The precipitate was washed with 10% potassium carbonate solution and then with water. The resulting off-white solid was dried overnight at 110° C. under a vacuum to give 0.42 g (86% yield) of poly(dodecane terephthalamide) with a relative viscosity of 1.81 in sulfuric acid.

What is claimed is:

1. A method of producing poly(terephthalamides) comprising the steps of:
   a) reacting 1,12-dodecanediamine or 1,14-tetradecanediamine with acid chloride of terephthalic acid to form cyclic diamides at a temperature below the melting point of the resulting cyclic diamides; and
   b) heating said cyclic diamides to form said poly(terephthalamide) to a temperature between the melting point of the cyclic diamide and about 330° C.

2. The method of producing poly(terephthalamides) according to claim 1, wherein said temperature of reacting said diamine with acid chloride of terephthalic acid is a temperature between about 0° C. and about 100° C.

3. The method of producing poly(terephthalamides) according to claim 1, wherein said cyclic diamide is heated at a temperature between about 275° C. and about 320° C.

4. The method of producing poly(terephthalamides) according to claim 1, wherein said cyclic diamides that are heated to form said poly(terephthalamides) further comprises up to 30 mol % of a metacyclic diamide synthesized from isophthalic acid and a n-alkylene diamine having 10 to 14 carbon atoms at a temperature below the melting point of the resulting metacyclic diamide.

5. The method of producing poly(terephthalamides) according to claim 4, wherein said metacyclic diamide is synthesized by reacting said n-alkylene diamine with acid chloride of isophthalic acid, t-butyl isophthalic acid or phenylindane dicarboxylic acid at a temperature between about 0° C. and about 100° C.

* * * * *